United States Patent
Kleiser et al.

(10) Patent No.: US 11,246,517 B2
(45) Date of Patent: Feb. 15, 2022

(54) APPARATUS FOR MEASURING OPTICAL PARAMETERS IN SCATTERING MEDIA

(71) Applicant: Universitat Zurich, Zurich (CH)

(72) Inventors: Stefan Kleiser, Grenzach-Wyhlen (DE); Martin Wolf, Zurich (CH); Daniel Ostojic, Zurich (CH); Nassimsadat Nasseri, Zurich (CH)

(73) Assignee: Universität Zürich, Zürich (CH)

( * ) Notice: Subject to any disclaimer, the term of this patent is extended or adjusted under 35 U.S.C. 154(b) by 106 days.

(21) Appl. No.: 16/757,490

(22) PCT Filed: Oct. 19, 2018

(86) PCT No.: PCT/EP2018/078764
§ 371 (c)(1),
(2) Date: Apr. 20, 2020

(87) PCT Pub. No.: WO2019/077133
PCT Pub. Date: Apr. 25, 2019

(65) Prior Publication Data
US 2021/0219881 A1 Jul. 22, 2021

(30) Foreign Application Priority Data
Oct. 20, 2017 (EP) ..................... 17001733

(51) Int. Cl.
*A61B 5/1455* (2006.01)
(52) U.S. Cl.
CPC .. *A61B 5/14552* (2013.01); *A61B 2562/0238* (2013.01); *A61B 2562/182* (2013.01); *A61B 2562/185* (2013.01)

(58) Field of Classification Search
CPC . A61B 5/1455; A61B 5/14552; A61B 5/0059; A61B 2562/0238; A61B 2562/182; A61B 2562/185
See application file for complete search history.

(56) References Cited

U.S. PATENT DOCUMENTS

| 4,830,014 A | 5/1989 | Goodman et al. |
| 5,109,849 A | 5/1992 | Goodman et al. |

(Continued)

FOREIGN PATENT DOCUMENTS

| WO | 2005010567 | 2/2005 |
| WO | 2010111127 | 2/2010 |

*Primary Examiner* — Eric F Winakur
(74) *Attorney, Agent, or Firm* — Volpe Koenig (57) ABSTRACT

A spectrophotometric apparatus for determining optical parameters in a scattering medium based on the measurement of attenuation of light propagating through said medium by diffusion. To eliminate the detrimental effect of light being guided in an intermediate optical layer between a surface of the medium and a contact surface of the apparatus, either a multitude of optical barriers may be formed in the contact surface or the angular range over which light is emitted or received by the apparatus may be limited by appropriate means. With both of these alternative approaches, light propagation in the intermediate layer can be suppressed, leading to increased measurement accuracy. This is particularly beneficial for building an oximeter with improved precision. Further aspects include features for improving the applicability of the apparatus on curved surfaces such as the strongly curved skulls of neonates.

20 Claims, 7 Drawing Sheets

(56) References Cited

U.S. PATENT DOCUMENTS

| | | | |
|---|---|---|---|
| 5,411,024 A | | 5/1995 | Thomas et al. |
| 5,661,302 A | | 8/1997 | Evans et al. |
| 5,779,631 A | | 7/1998 | Chance |
| 5,995,856 A | * | 11/1999 | Mannheimer ...... A61B 5/14552 600/322 |
| 6,078,833 A | | 6/2000 | Hueber |
| 6,321,100 B1 | * | 11/2001 | Parker ................ A61B 5/14552 600/340 |
| 6,526,300 B1 | * | 2/2003 | Kiani ................ A61B 5/14552 600/322 |
| 6,845,256 B2 | * | 1/2005 | Chin .................. A61B 5/14552 600/323 |
| 8,055,321 B2 | | 11/2011 | Bernreuter |
| 8,460,197 B1 | | 6/2013 | Brady et al. |
| 2006/0241502 A1 | | 10/2006 | Chance |
| 2009/0171177 A1 | | 7/2009 | Hannula et al. |
| 2009/0259114 A1 | | 10/2009 | Johnson et al. |
| 2013/0060259 A1 | | 3/2013 | Porat |
| 2013/0077095 A1 | | 3/2013 | Besko |
| 2014/0364707 A1 | * | 12/2014 | Kintz .................. A61B 5/1459 600/310 |
| 2016/0143537 A1 | | 5/2016 | Dalene |
| 2018/0228414 A1 | * | 8/2018 | Shao ................ A61B 5/14552 |

\* cited by examiner

APPARATUS FOR MEASURING OPTICAL PARAMETERS IN SCATTERING MEDIA

TECHNICAL FIELD

The invention concerns an apparatus for measuring optical parameters in a scattering medium, comprising at least one light source emitting at least one wavelength and at least one detector for detecting said wavelength, wherein said at least one light source and said at least one detector emit and receive light, respectively, through a contact surface being in contact with a surface of the medium during a measurement.

In particular, the invention relates to the field of spectrophotometry and oximetry, which aims at measuring optical properties and deriving parameters such as oxygen saturation in living tissue. Spectrophotometry allows determination of optical properties such as absorption and scattering coefficients by illuminating a specimen and determining the attenuation in light intensity over distance. Oximeters are apparatuses that make use of spectrophotometry for determining the (arterial, venous or mixed) oxygenation of blood in tissue.

BACKGROUND

A special spectrophotometric method is Near-Infrared Spectroscopy (NIRS), which determines concentration of chromophores (for example oxy- and deoxyhemoglobin) in human tissue and, derived from these concentrations, tissue oxygen saturation (StO2). This is accomplished by illuminating the tissue at one or more spots with multispectral sources and measuring the received light intensity at one or more distant points. For this purpose, state-of-the-art oximeters use photodiodes as detectors and various LEDs with different emission wavelengths as light sources.

In a turbid medium such as human blood, scattering is dominant and light transport can be modelled by a diffusion process. As an important consequence, it is possible to measure blood oxygenation in human tissue with NIRS not only in transmission but also in reflection mode.

When modeling a reflective NIRS-measurement of human tissue, typically semi-infinite boundary conditions are assumed. This means that photons reaching the skin surface are assumed to be lost for the measurement. For curved surfaces, adequate corrections can be applied.

If one or more light sources and two or more light detectors (or 2+ sources and 1+ detectors) are used, then a multi-distance algorithm can cancel out many factors requiring calibration in a simple one-source-one-detector-setting. Such an algorithm, however, requires coupling and instrumental factors to be equal for the multiple elements (for example for two detectors in a one source and two detector setting). Furthermore, with 2+ sources and 2+ detectors a self-calibrating algorithm can be used (for example as described in U.S. Pat. Nos. 6,078,833, 5,661,302, or U.S. Pat. No. 8,055,321) cancelling out all instrumental and optical coupling factors.

Despite these sophisticated measurement approaches, state-of-the-art oximeters are still plagued by insufficient precision and accuracy, which are major road-blocks for wide-spread clinical use. This is particularly true for oximeter measurements performed on the foreheads of neonates.

SUMMARY

It is therefore an object of the present invention to provide an apparatus for measuring optical parameters in a scattering medium, in particular an oximeter, with improved precision and accuracy. It is a further object of the present invention to provide an oximeter that is particularly adapted to performing measurements on the foreheads of neonates. It is yet another object of the present invention to improve the sensitivity of the apparatus to deep layers of the medium.

In accordance with the present invention, an apparatus is provided which solves the afore-mentioned problem. In particular the invention proposes an apparatus as introduced at the beginning, which, in addition, is characterized in that on or in said contact surface, at least two optical barriers are arranged such that propagation of said wavelength through a layer between the contact surface and the surface of the medium is suppressed. This apparatus may be used for accurately determining optical properties of virtually any scattering medium, in particular when the medium has a soft surface.

As already explained, in particular algorithms for reflective NIRS measurements on human skin typically assume that all light emitted by a source and reaching a detector has travelled through the human tissue. In typical measurement situations, however, there is a layer present between the skin and the lower contact surface of the oximeter. This layer may be composed of air and/or sweat and/or grease. In this case, at least part of the light emitted by a source of the oximeter can reach a detector by propagating through the layer through multiple reflections at the boundaries of the layer. In other words, this part of the emitted light reaches the detector without having travelled through tissue at all or only partly. This effect, which is referred to as "light piping" in the following, creates a measurement error of unknown quantity and affects measurement precision negatively. In the worst case, light piping may completely invalidate the measured StO2, in particular if the layer is thick.

As a major benefit of the invention, the proportion of photons reaching the detector and having travelled completely or at least partially not in the scattering medium (e.g. tissue) but instead in the layer can be minimized. Since such photons create false measurements, which cannot be canceled out by exploiting known boundary conditions or using automated calibration algorithms, the accuracy of the measurement can be improved significantly, compared to the state of the art.

Oximeters known in the state-of-the-art typically feature a planar, i.e. completely flat, contact surface. Light sources and detectors typically send out and receive light through transparent windows embedded in the contact surface. Such sensors, which are typically used only one time, are pressed against the skin or attached using an adhesive film to achieve good light coupling into the tissue. However, very often these types of sensors show only unsatisfactory precision and accuracy. A major reason is light piping occurring in the unavoidable layer between the contact surface of the oximeter and the skin.

According to the invention, the optical barriers can constrict the light channel made up by the layer or, in the best case, they can block light propagation in the layer completely. Thus, propagation of said wavelength through the layer is effectively suppressed.

An optical barrier according to the invention may be made of any structure that blocks and/or redirects and/or impedes propagation of said wavelength through the layer. For this purpose, the optical barrier may block, reflect, redirect, trap, or absorb said wavelength, in particular after propagation inside the layer. In other words, according to the invention an optical barrier may be formed as a wall or ridge, a depression, an optical trap (e.g. light capturing material or opening) or as a mirror or any other optical structure redirecting light.

When measuring in human tissue, as an example, which is highly scattering, the photons emitted by a source diffuse away from that source. This means that all the way between the source and a detector there are photons reaching the skin surface, likely leaving it. In fact, for a homogenous semi-infinite and turbid medium illuminated by a point source, at any point the highest photon density is directly at the surface. As not all of these photons are absorbed by the contact surface after leaving the tissue, some of these photons may pass all or part of the remaining distance to the detector outside of the tissue, thus violating the semi-infinite boundary condition, on which the measurement algorithm is based. As a consequence, poor measurement precision is observed.

The invention solves this problem by arranging in or on said contact surface a multitude of optical barriers, preferably between said at least one light source and said at least one detector. Thus, even if light emitted by said source circumvents a first optical barrier by initially propagating through tissue and leaving the surface afterwards to re-enter the layer, such light can be effectively stopped by a second optical barrier of said multitude of optical barriers. In consequence, a minimum of two optical barriers is required according to the invention to achieve effective suppression of light piping.

For example, in most measurement situations of an oximeter, a single optical barrier arranged around a detector will be insufficient for improving measurement accuracy. This is because light reaching this final optical barrier in front of the detector may have already traveled a long way in the layer by multiple reflections. Thus, photons having been light-piped for some distance in the layer and reaching the skin surface just in front of the optical barrier may enter the tissue and, after diffusion through the tissue, finally reach the detector. Although such photons have travelled some distance within tissue, they contradict the underlying assumption that all photons reaching the detector have exclusively traveled through tissue. Hence such photons will create false measurements. According to the invention, such false measurements may be prevented by effectively blocking photons traveling through the layer between oximeter and skin, using a multitude of optical barriers.

Another, unwanted effect of photons emitted by the surface of the medium and re-entering said light guiding layer between the surface of the medium and the contact surface of the apparatus is that more photons reach the detector, which have passed mainly through superficial layers of the medium (violating the assumption, that every photon reaching the surface is absorbed). Thus the apparatus is more sensitive to superficial layers and less sensitive to deeper layers of the medium. In particular for oximeters, such a characteristic is a severe practical drawback, since the oxygenation of deeper tissue layers is of primary clinical relevance.

To improve the sensitivity of the apparatus to deep layers of the scattering medium, for example to tissue layers which are deeper than 5 mm from the skin, a preferred embodiment of the invention suggest to arrange at least three, preferably at least four optical barriers in or on said contact surface, in particular between said at least one light source and said at least one detector. This way, propagation of said wavelength in the layer can be strongly suppressed. Hence, in particular if the medium shows a high absorption of said wavelength such that only a small number of photons reach the detector after having traveled through the tissue by diffusion, this number will still be higher than the number of photons reaching the detector and having propagated through the layer by light piping.

The general concept of the invention disclosed herein is to effectively suppress propagation of said wavelength through the layer between the contact surface and the surface of the medium.

Following this inventive concept, the afore-mentioned problem is solved alternatively by an apparatus with one or more features described herein. Thus, the invention also proposes an apparatus as introduced at the beginning, which, in addition, is characterized in that the apparatus comprises means for limiting angles at which light rays emitted by said at least one light source exit said contact surface and/or at which light rays received by said at least one detector re-enter said contact surface such that propagation of said wavelength through a layer between the contact surface and the surface of the medium is suppressed. Such means may be, for example, apertures, in particular a single slit aperture or multiple slit apertures, and/or lenses, for example a single cylindrical lens or multiple cylindrical lenses. To achieve a substantial suppression of light piping in the layer, it is preferable, if said angles are limited to less than +/−30°, most preferably to less than +/−15°. Hence, for example the refractive power of the lens or the location and/or size of the respective aperture may be chosen with respect to a light receiving or light emission cone of a respective detector or source, respectively.

Propagation of the measurement wavelength in the layer results from multiple (internal) reflections at the boundaries of the layer. Such reflection, however, only occur, if light rays are incident on the boundaries at large angles. Otherwise, the light is not guided by the layer but enters the scattering medium, which is desirable for an accurate measurement. By employing means which limit the emission angles of the at least one light source as described above, it is thus possible to prevent a large portion of light emitted by said light source to propagate in the layer between the contact surface of the apparatus and the surface of the medium.

On the other hand, if the detector is only capable of detecting light rays within a small angular range, light guided in the layer at large reflection angles can no longer reach the detector. Therefore, it is possible to effectively suppress the detrimental effect of light piping also by limiting the range of angles, at which said at least one detector can receive light rays. In this respect, it is important to note that light having traveled by diffusion through the scattering medium is re-emitted by the surface of the medium below the detector over a large angular range, which will also cover the angular range accepted by the detector. Thus only unwanted propagation of light through the layer and up to the detector is effectively suppressed, while light used for the measurement can still reach the detector.

According to the invention, it is of particular advantage to combine the features of the apparatuses described above, respectively. This is because the advantageous effects of both alternative implementation of the general inventive concept may combine to further improve measurement accuracy.

According to the invention, there exist further advantageous embodiments solving the aforementioned problems, which are described in the sub-claims and in the following.

For example, one embodiment suggest to use the apparatus described herein as an oximeter for measuring tissue oxygenation. In this case, the contact surface is the surface with which the apparatus rests on the skin or another tissue surface. For example, the surface on which the apparatus is placed can be the surface of an internal organ. Thus, the apparatus described herein may also be useful for determining the oxygenation of transplanted organs during or shortly after transplantation. In particular, the oximeter according to the invention can be employed for measuring oxygenation in cerebral tissue of neonates. In all of the above situations, the scattering medium may be living tissue.

Employing one detector and two different wavelengths emitted by at least one light source, the relative oxygenation may be determined. Hence, it can be of advantage if said at least one light source emits at least two different wavelengths. Accordingly, said optical barriers or said means may be arranged such that propagation of said at least two different wavelengths through the layer is suppressed. This may be achieved by designing the means and/or the barriers such that they have an optical effect on all of the at least two wavelengths.

Specifically, the invention therefore also concerns an oximeter for measuring tissue oxygenation comprising at least one light source emitting at least two different wavelengths, at least one detector for detecting said wavelengths, wherein said at least one light source and said at least one detector emit and receive light, respectively, through a contact surface being in skin contact during a measurement.

According to another embodiment of the invention, said optical barriers may be arranged between said at least one light source and said at least one detector. By placing the barriers in between light source and detector, it is possible to stop propagation of light in the layer, even when such light has circumvented an first optical barrier by traveling through the medium.

Following this logic, it is preferable when said optical barriers interrupt a line-of-sight along the contact surface between said at least one light source and said at least one detector at least twice, preferably at least three times, most preferably at least four times. By such an arrangement, the probability of successful light piping from the light source to the detector is greatly reduced.

It is not recommended to use large area plateaus as optical barriers, since in this case, a flat layer will build up below the plateau. Hence, the efficiency of suppressing light propagation in the layer will not be increased by using a large area. Instead, using a high spatial frequency of optical barriers is considered to be most efficient.

As the line-of-sight, as used in the description above, the direct path along the contact surface may be considered, which runs from a first point, where photons of the light source exit the contact surface, to a second point where photons re-enter the apparatus (typically through a window) to finally reach the detector. For a flat contact surface, the line-of-sight will thus be identical to a corresponding source-detector-separation.

For improving the accuracy of the measurement, it may be desirable to employ multiple source-detector-separations. For example, when using two detectors and two different measurement wavelength emitted by at least one light source or one detector and two different wavelengths emitted by at least two light sources (spaced apart from each other), absolute oxygenation in tissue can be measured. In other words, such configurations are characterized in that a minimum of two different optical path lengths between a light source and a detector and two different measurement wavelengths can be employed in the measurement. In such a setting, accurate estimations of the absolute oxygenation in tissue can be obtained by measuring light attenuations of the at least two wavelengths over distance.

Accordingly, a favorable/advantageous embodiment of the invention suggests that the apparatus comprises at least two light sources and/or at least two detectors such that the apparatus features at least two different line-of-sights which may be used during a measurement. In such a configuration, it can be preferable that said at least two light sources and/or said at least two detectors are positioned apart from each other, respectively. Further, for improved accuracy it is of advantage if said optical barriers interrupt each of the at least two different line-of-sights at least once, preferably at least twice. Most preferably, all line-of-sights, in particular those employed during a measurement, may each be interrupted by said optical barriers at least once, preferably at least twice.

According to another embodiment, said optical barriers may be formed as walls or ridges protruding from said contact surface. In this case, the height of said optical barriers above said contact surface should be less than 5000 µm.

Preferably the height should be less than 1000 µm, and most preferably less than 500 µm. Such a dimensioning ensures that the optical barriers are robust and that the apparatus can be brought in stable contact with the surface of the medium, such that the measurement position and/or coupling efficiency does not change during a measurement. Using a height of less than 1000 µm has the advantage of easy disinfection. Surprisingly, a height of less than 500 µm can still be sufficient for optical attenuation of light piping, as long as the skin can penetrate in between the optical barriers. This will be the case, for example, if the spatial frequency of the barriers is in the order of 1 barrier/mm.

On the other hand, to achieve a substantial suppression of light piping, the height of said optical barriers above said contact surface should be more than 10 µm, preferably more than 50 µm. Such values ensure that the optical layer will show a significant curvature, due to the corrugation resulting from such barriers. Typically, a height of 10 µm will be only sufficient, if the medium to be measured has an especially soft surface.

While the cross-section of a single optical barrier may be preferably uniform, the course and/or cross-sections and/or height of neighboring optical barriers can be varied, to optimize the arrangement or mechanical and optical properties of the optical barriers.

The apparatus disclosed herein may also be used as a multiple-times-of-usage-oximeter. In this case it is of advantage, if said optical barriers are shaped exclusively with angles of more than 90°, preferably exclusively with rounded edges. This allows easy cleaning and reliable disinfection of the apparatus.

With respect to the orientation of the optical barriers, it is preferred if, at points of intersections between an optical barrier and a line-of-sight, said optical barriers are oriented at an angle to the respective intersecting line-of-sight. Preferably, this angle of intersection may have a value of more than 45°, since in such an orientation, the suppression of light propagation in the layer is most efficient.

According to yet another embodiment, the optical barriers should show an aspect ratio and/or should be spaced apart from each other such that, when the apparatus is placed on the surface of the medium, i.e. in particular on skin, during a measurement, the surface (in particular skin) can penetrate in between said optical barriers. As a result of such a spacing, the surface/the skin can follow the profile of the optical barriers such that the resulting optical layer between the apparatus and the surface/the skin will no longer be flat but corrugated. According to the invention, light piping in such a corrugated layer is greatly reduced as compared to that in a flat layer, since it is far more likely that light enters the medium/the tissue when hitting a sharply curved surface of the medium/the tissue.

Preferably, the optical barriers should be formed such that the surface/the skin touches the contact surface in between said optical barriers. This way, the light channel made up by the layer may be squeezed repeatedly by the optical barriers. In this respect it is of particular advantage, if said optical barriers are soft and/or flexible, because this improves a close contact between the barriers and the surface/the skin.

If the optical barriers are too slim, however, they may lack robustness during use or insufficient optical absorption. Moreover, pressure marks can result on the skin of a patient after a measurement, leading to skin peeling and subsequent infections. On the other hand, the apparatus may become difficult to clean and less convenient to apply on curved surfaces, if the barriers are too broad. Hence, to achieve a good compromise between efficient suppression of light piping, good adaptability of the apparatus on soft surfaces and ease of use, one embodiment suggests that the optical barriers should show a width in a direction of a corresponding line-of-sight of more than 100 µm, preferably more than 200 µm, most preferably more than 300 µm. Based on the above considerations, it may also be preferable that said width is less than 2.5 mm, preferably less than 1.5 mm.

Embodiments as described before may be achieved by forming said optical barriers as corrugations, preferably with constantly spaced ridges. As examples, such corrugations may resemble a succession of rectangular pulses or be formed in the shape of a sine wave. In the latter case, one half of the sine wave may be considered as constituting the optical barriers, while the other half of the sine wave may be considered as acting as the contact surface. As an important advantage of such an embodiment, the skin may easily follow such, preferably smooth, corrugations, resulting in a layer between the contact surface and the medium that follows the shape of the corrugations. Hence, the layer may no longer be flat and light propagation in the layer is thus further impeded. In addition, a high repetition rate of the barriers and good adaptability of the apparatus may be achieved.

Likewise, it may be of advantage, if a minimum distance between neighboring optical barriers is larger than a height of said neighboring optical barriers. Thus, an aspect ratio of less than 1:1 is considered beneficial for achieving efficient suppression of light piping.

According to another advantageous embodiment, said optical barriers can be made from a material which absorbs said wavelength. Alternatively or additionally, said material may be porous or a surface of said optical barriers may be rough and/or optically matt. In like manner, the contact surface of the apparatus, in particular in between said optical barriers, may be porous and/or optically matt and/or may absorb said wavelength. All of these particular features are highly beneficial for impeding light propagation through the layer either by absorbing, scattering or trapping light, respectively.

The optical barriers discussed herein may be formed at various distances from each other. Thus along a line-of-sight between a source and a detector, optical barriers may be placed in various duty cycles. For example, the width and distances of individual opaque ridges forming the optical barriers may be varied. However, to optimize the suppression of light piping, it is suggested that at least 10%, preferably at least 30%, most preferably at least 50%, of a line-of-sight along the contact surface is occupied by said at least two optical barriers. As light may re-exit the surface even after having travelled through the medium below a first and a second optical barrier, it is of particular advantage if the proportions of the line-of-sight stated above may be occupied by at least three individual optical barriers. In the latter case, the line-of-sight between the light source and the detector may thus be interrupted at least three times, while the widths of the at least three optical barriers may sum up to the fraction of the length of the line-of-sight stated above.

According to another embodiment of the apparatus disclosed herein, said at least one light source and/or said at least one detector may emit and receive photons, respectively, through windows embedded in said contact surface. For such embodiments, it is suggested that said optical barriers are spaced apart from said windows, in particular in a direction of a corresponding line-of-sight. By such an arrangement, the surface of the medium (e.g. skin) can bend towards the window and thus come into much closer vicinity to the windows, as would be the case when placing the optical barrier directly at the edge of the window. As a result, the light emitted through the window will be more likely to enter the medium (e.g. tissue) than to enter the light guiding layer, such that light piping is suppressed.

According to another embodiment, at least one of said windows may additionally feature a transparent ridge facing the surface, in particular skin. This transparent ridge should run in a direction transverse, preferably approximately perpendicular, to a main direction of propagation of said photons, which are emitted by the light source and reach the detector. Furthermore, it is preferable if some of the optical barriers merge into said transparent ridge. In this case, it is desirable that the optical barriers merging into said transparent ridge share a common cross-section with that transparent ridge, favorably along their full length.

The transparent ridges just described do not suppress the propagation of photons emitted by a light source and/or received by a detector. However, similar to the teeth of a comb, the transparent ridges, preferably in conjunction with the optical barriers, can be used to comb the hair of a patient into a common direction, when placing the oximeter on the skin of the patient. By combing the hair with the contact surface of the oximeter, using the corrugation resulting from the optical barriers and from transparent ridges on the windows, the hair can be orientated in a direction transverse to the main direction of propagation of the measured photons. Such an orientation is highly advantageous, since a single hair, in particular in the case of light hair, can act as a light guide, resulting in massive light piping similar to that occurring in the transparent optical layer described above. By orientating the hair in a direction transverse to the propagation direction of detected photons, light may still be guided in the hair but in a direction away from the detector such that this light can no longer reach the detector. As a result, measurement errors resulting from light piping in the hair of the patient are greatly reduced.

To optimize and facilitate such combing with the contact surface of the apparatus, one advantageous embodiment of the invention proposes to form gaps between optical barriers and/or between optical barriers and a transparent ridge. For optimum results, said gaps should run continuously and uninterruptedly in a direction transverse to a main direction of propagation of photons detected during a measurement, preferably over a full width of the contact surface. Most preferably, a width of said gaps may be at least half of a width of said optical barriers. Such a size is considered sufficient for supplying enough room for the hair filling those gaps after combing the hair by stroking over the skin of the patient with the contact surface of the oximeter.

Referring to the second alternative implementation of the general inventive concept, in a preferable embodiment said means are oriented such that the angles, at which light rays emitted by said at least one light source exit said contact surface and/or at which light rays received by said at least one detector re-enter said contact surface, are limited, in particularly exclusively, in a direction of a corresponding line-of-sight. Thus, perpendicular to that line-of-sight, said angles may be larger or may not be limited at all. The underlying reasoning for such an embodiment is that for suppressing light propagation through the layer between the contact surface and the surface of the medium, it is sufficient to limit the angles in the direction of the line-of-sight. In fact, illuminating a broad area using large emission angles in a direction perpendicular to a corresponding line-of-sight may actually be beneficial, because a large volume of the medium can be illuminated, which can improve accuracy and robustness of the measurement.

For achieving an unilateral limitation of emission or reception angles as described above, said means may be slit apertures or cylindrical lenses or a combination of both. Also, a single slit aperture or a single cylindrical lens may be used. In all of these cases, the cylindrical lenses and/or slit apertures should be oriented transversal to said corresponding line-of-sight. Hence, for a slit aperture, the longer dimension should be transversal to the line-of-sight, while a cylindric lens should only focus light in the direction of the line-of-sight. To reduce the loss in light intensity when using slit apertures, the aperture and/or a cavity surrounding the light source may be coated with a reflective or white material.

When using multiple sources, in particularly if they are linearly arranged, the lenses or apertures may be arranged such that light emitted from neighboring light sources of the apparatus overlaps on the surface of the medium. This way, at least part of the light emitted by different light sources may travel identical paths through the underlying medium, which is beneficial for obtaining accurate measurements.

When using slit apertures, these may be located inside the apparatus, in particular at a distance from the windows embedded in the contact surface, already described above. Most preferably, the slit apertures should be located such that the slit aperture and not the window determines the light cone emitted by a light source or received by a detector. This implies, that the slit aperture should be smaller than an aperture defined by a corresponding window. For example, if the window is made from a transparent silicone, the relative position of the window to the light source may change during a measurement, due to applied bending or pressure. In such a case, a smaller inner slit aperture guarantees that the light pattern on the skin remains the same during a measurement, as the inner aperture is unaffected by bending or pressure.

To improve the overall performance and measurement accuracy of the apparatus, sources as well as detectors may be individually shielded against electromagnetic interference (EMI). In particular, the at least one light source and/or the at least one detector of the apparatus may be covered by an electromagnetic (em-)shielding. The em-shielding may overlap and/or laterally cover the respective source/detector. In fact, for best performance the em-shielding should cover the respective source/detector and other electronic components in direct vicinity of the respective source/detector. The em-shielding may consist of a single part or multiple parts.

In particular the apparatus may feature several separate em-shieldings, each one covering one respective or several respective electronic components, in particular a light source and/or a detector. Of course, an em-shielding according to the convention may also cover several electronic components in particular two or more sources and/or detectors.

To allow light to be emitted from a source or to reach a respective detector, the em-shielding may have an opening or repeated perforations, through which light can pass. One very convenient way is to employ an em-shielding in the form of a perforated mesh, e.g. a net of wires with reasonably low filling ratio. The em-shielding can be made from a conductive material or from an insulating material featuring a conductive coating.

In case the respective source/detector is mounted on a printed circuit board (PCB), it is convenient, if the em-shielding is electrically connected with an electrical potential provided by the PCB. For example, the em-shielding may be attached to a contact pad on the PCV by soldering, conductive glueing, welding or like means. Typically, the shielding may thus be on one well-defined electrical potential, e.g. on ground potential. In this case, any short-circuiting between the em-shielding and electronic components on the PCB must be avoided. During measurements, pressure is typically applied on the apparatus and thus, a force may be acting on the em-shielding with the danger of bringing a conductive part of the em-shielding in contact with an electronic component on the PCB, resulting in a short-circuit. To solve this issue, one particular embodiment of the apparatus proposes that the em-shielding is insulated from said source/detector, at least to those parts with an electrical potential different from the potential of the em-shielding. Such insulation may be preferably achieved by a non-conductive frame or the like. Another possible solution of similar insulation quality proposes that an air-gap is formed between the em-shielding and the components and/or source/detector. In this case, the em-shielding should have a sufficient rigidity to maintain the air gap during normal operation of the apparatus.

As has been discussed before, it may be of great advantage to employ one or several slit apertures, each one positioned above a source/detector to limit the angles at which light is emitted/received by the respective source/detector. For obtaining optimum optical as well as electronic performance as well as a compact size of the apparatus, it is suggested in such a case that the slit apertures are positioned within the em-shielding. This may be achieved for example, if said slit apertures are located in between said at least one light source/said at least one detector and the electromagnetic shielding. Additionally or alternatively, said slit apertures may be formed by the em-shielding itself. The latter approach also reduces the fabrication cost. For example, the slit aperture may be formed by a conducting material or by a conductive coating, and thus effectively act both as an optical aperture and as an em-shielding. Such a slit aperture, with or without em-shielding functionality, can be manufactured for instance by laser-cutting, etching or milling.

One particular embodiment proposes that the em-shielding consists of a box formed from a metal sheet and with a slit aperture formed in the metal sheet. Such a shielding provides both optical functionality and very high shielding against EMI and can be conveniently mounted onto a PCB, in particular by soldering. According to yet another advantageous embodiment, all, or a subset, of the light sources and detectors of the apparatus may be linearly arranged along a longitudinal axis. In this case, it is particularly preferable, when the at least two detectors of the apparatus described above are arranged on said longitudinal axis. In such a linear arrangement, for photons emitted by any of said linearly arranged light sources and reaching one of said detectors, a main direction of propagation may coincide with said longitudinal axis. For such embodiments, the invention suggests to orient all optical barriers at an angle of intersection of more than 45° to said longitudinal axis. By such arrangements it can be guaranteed, that efficient suppression of light piping is achieved for multiple light sources employed during a measurement.

According to the invention, a linear measurement approach using multiple source-detector-separations can be further improved, if the optical barriers show a lateral length in a direction transverse to a main direction of propagation of photons used during a measurement that is larger than a maximum transverse separation of light sources of the apparatus. In this case, efficient suppression of light piping can be achieved even for those light sources, which show the largest distance to the longitudinal axis of the linear measurement arrangement.

However, the present invention is also applicable to two-dimensional non-linear arrangement of sources and detectors. For example, for spatially determining tissue oxygenation, a central detector may be used in conjunction with light sources arranged on a circle being concentric to the central detector. Alternatively, a central light source may be used with several detectors arranged in various directions and/or at various distances from the central light source. In such arrangements, there is no major direction of light propagation but several major directions of light propagation. Nevertheless, using a multitude of optical barriers for interrupting individual line-of-sights between a light source and a detector as described herein may be advantageously applied to such non-linear arrangements as well.

When using sheet-like state-of-the-art oximeters, which often show a rectangular shape of the contact surface, it is often impossible to achieve a close contact of the entire contact surface with the skin, in particular when measuring on the tiny and strongly curved skull of neonates. In order to tackle this problem, the invention suggests that the apparatus, which may be employed as an oximeter, should be highly bendable at least around one axis, preferably around two perpendicular axes.

To achieve this goal, one embodiment suggests that at least the contact surface of the apparatus is bendable and/or flexible, preferably along two perpendicular axes. This may be achieved, for example, by forming the contact surface by a main body of a, preferably soft and/or biocompatible material, for example silicone or polyurethane. Preferably, the material of the main body should also be opaque to said wavelength.

Said main body may also carry and/or encapsulate said at least one light source and/or said at least one detector. Even more of advantage, the main body may also form said optical barriers and/or the slit apertures described before.

Additionally or alternatively, the main body may also features thinnings, either on a side opposite to said contact surface but preferably in the contact surface, to increase the bendability of the apparatus. For this purpose it is most preferable when said thinnings run across the full width of the apparatus in a transversal direction (with respect to a longitudinal direction in a linear measurement arrangement).

Finally, according to yet another embodiment, the applicability of the apparatus on soft and curved surfaces can be improved, if the contact surface, in its relaxed equilibrium state, shows a first curvature along a first axis of the apparatus. This first axis may be a transversal axis of the apparatus. By using such a pre-curvature, the forces acting on the apparatus when applying it on curved surfaces can be greatly minimized. To this goal, it is of further advantage, if the contact surface shows a second curvature along a second axis. This second axis can be the longitudinal axis described before. To achieve optimum applicability on the skull of neonates, the second curvature should have a radius of curvature R of approximately 4 cm.

BRIEF DESCRIPTION OF THE DRAWINGS

Preferred embodiments of the present invention shall now be described in more detail, although the present invention is not limited to these embodiments: for those skilled in the art it is obvious that further embodiments of the present invention may be obtained by combining features of one or more claims with each other and/or with one or more features of an illustrative embodiment described or illustrated herein. With reference to the accompanying drawings, where features with corresponding technical function are referenced with same numerals even when these features differ in shape or design:

DETAILED DESCRIPTION

Figure 1:
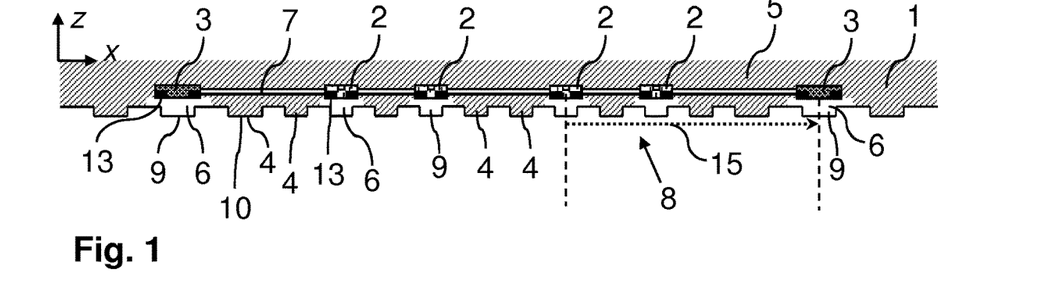
FIG. 1 is a partial cross-sectional side view of the oximeter of FIG. 2 along its longitudinal axis x.
Figure 11:
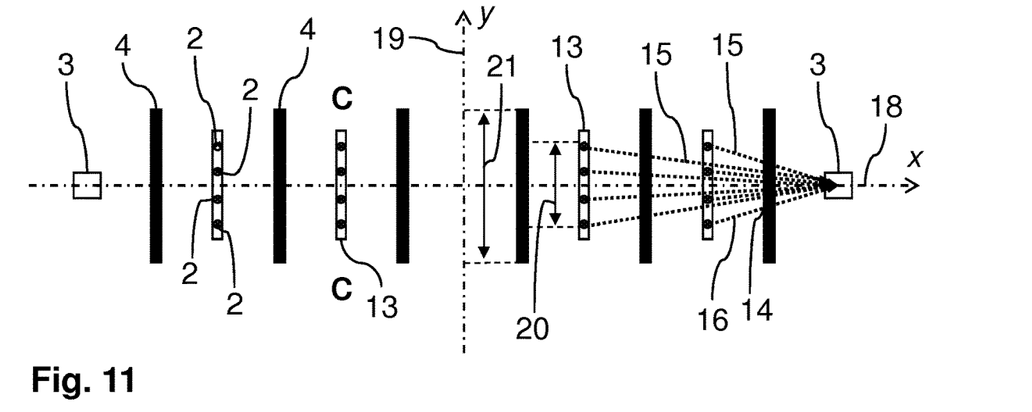
FIG. 11 is a schematic and simplified sketch of the layout corresponding to the top view of the oximeter of FIG. 2.

FIG. 1 depicts a partial cross-sectional side view of an oximeter 1 according to the invention, which may be used for measuring oxygen saturation in cerebral tissue of neonates. This apparatus 1 comprises a total of 16 light sources 2 emitting a total of four different wavelengths and two detectors 3 for detecting said wavelengths. The light sources 2 and detectors 3 are placed along a longitudinal axis x 18 on a printed circuit board 7 embedded in a main body 5 (c.f. FIG. 11) of the oximeter 1. Following the right upper dotted arrow in FIG. 2, indicating a direct line-of-sight 15 between the illustrated upper light source 2 and the right outermost detector 3, it is obvious that any photon traveling from this source 2 to that detector 3 is mainly propagating along the x-axis 18 and only partly along the y-axis 19. Thus, for the oximeter 1 of FIG. 2 featuring a linear arrangement of sources 2 and detectors 3, the main direction of propagation of photons used in the measurement (i.e. photons emitted by a light source 2 and detected by a detector 3) coincides with the longitudinal x-axis 18 of the oximeter 1.

Figure 25:
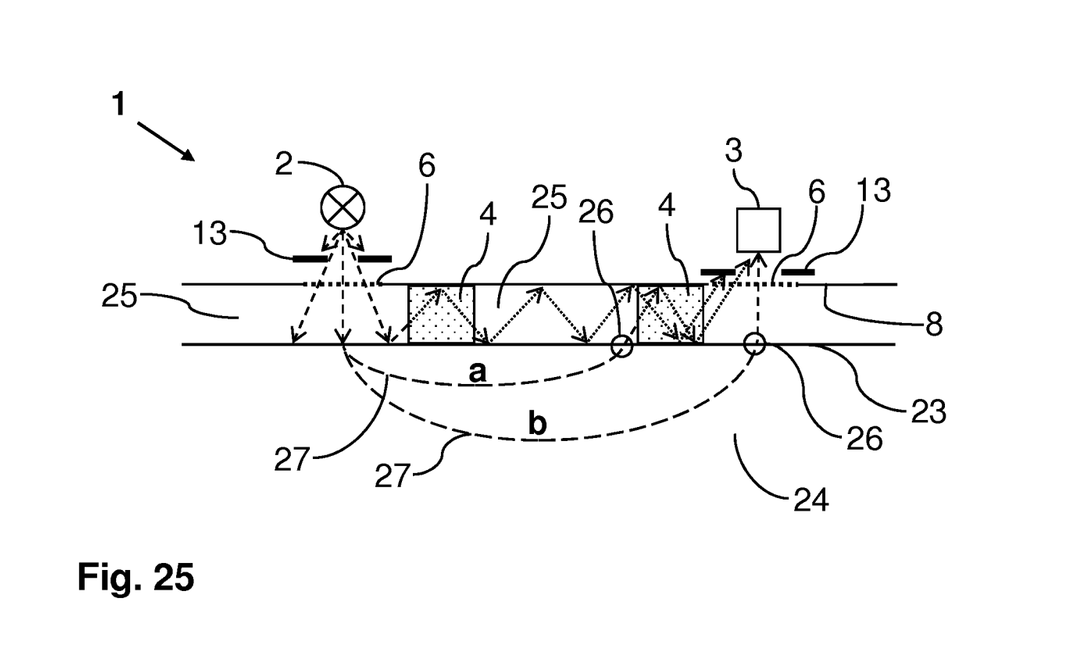
FIG. 25 illustrates the suppression of light piping by using ridges of rectangular cross-section as optical barriers.

During a measurement, the oximeter 1 is placed on the skin 23 with its lower contact surface 8, as illustrated in FIG. 25. As the printed circuit board 7 shows some flexibility and the main body 5 is made from highly elastic silicone, the contact surface 8 of the oximeter can be easily bent along two perpendicular axis (x-axis and y-axis in FIG. 2), allowing close contact to the skin 23. The indentations 17 illustrated in FIG. 2 facilitate twisting and bending of the oximeter 1.

Figure 6:
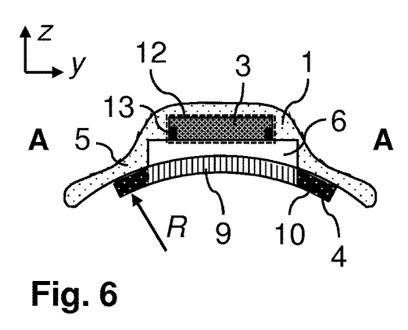
FIG. 6 is a full cross-sectional side view of the oximeter of FIG. 2 along its transverse axis y at the position A-A.
Figure 7:
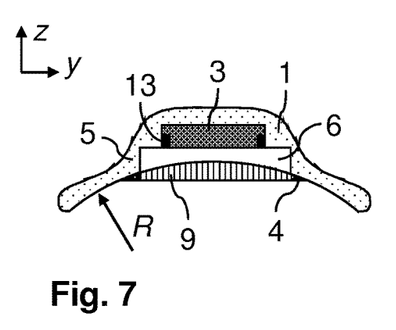
FIG. 7 is a full cross-sectional side view of another oximeter according to the invention.
Figure 8:
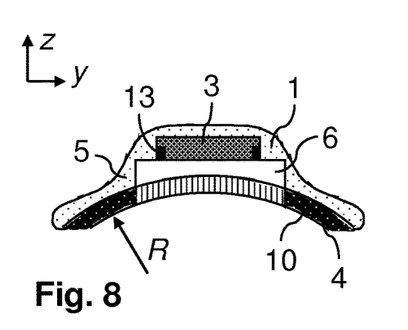
FIG. 8 is a full cross-sectional side view of yet another oximeter according to the invention.
Figure 9:
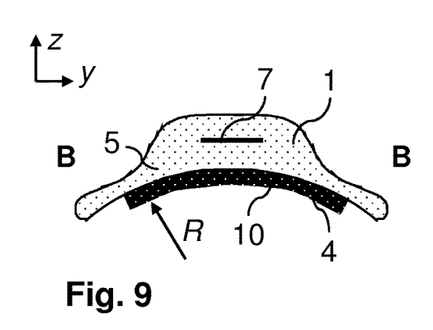
FIG. 9 is a full cross-sectional side view of the oximeter of FIG. 2 along its transverse axis y at the position B-B.
Figure 10:
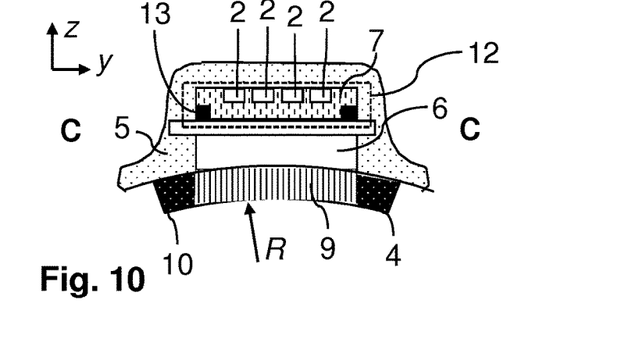
FIG. 10 is a full cross-sectional side view of the oximeter of FIG. 2 along its transverse axis y at the position C-C.

When no forces are applied, the contact surface 8 shows a radius of curvature R of approximately 4 cm (similar to the curvature of the heads of neonates at 27 weeks of gestational age) in the transverse direction y, as illustrated in FIGS. 6, 9 and 10. This feature ensures a good applicability of the oximeter 1 in particular on the small foreheads of neonates.

Figure 2:
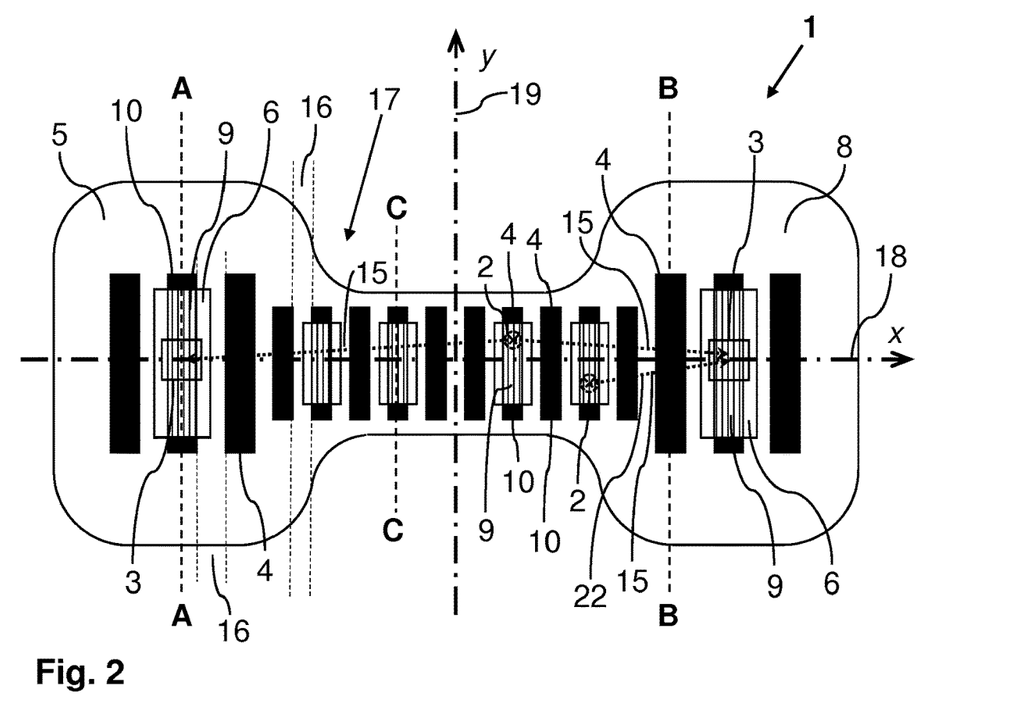
FIG. 2 shows a top view on the contact surface of an oximeter according to the invention.
Figure 3:
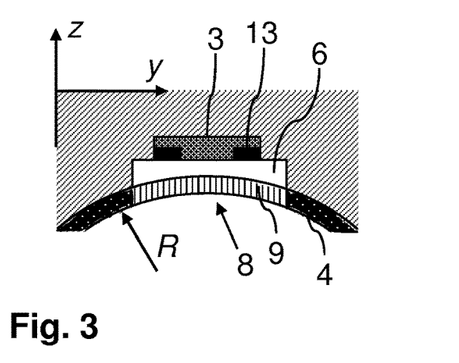
FIG. 3 illustrates a partial cross-sectional side view of an oximeter according to the invention.
Figure 4:
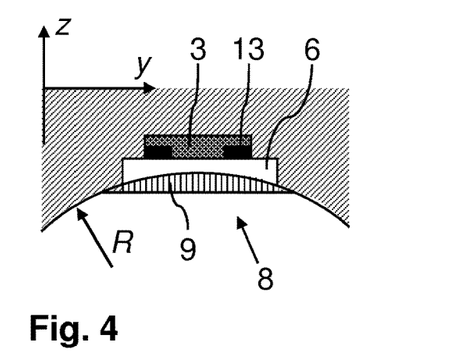
FIG. 4 depicts a partial cross-sectional view of yet another oximeter according to the invention.
Figure 5:
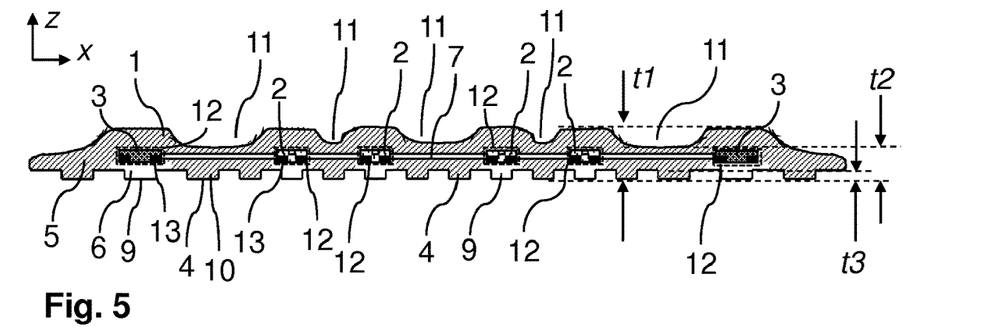
FIG. 5 illustrates a full cross-sectional side view of the oximeter of FIG. 2 along its longitudinal axis x.

The lower contact surface of the oximeter 1, which is designed in the shape of a dumbbell, is detailed in FIG. 2. Since the main body 5, which also forms the contact surface 8, absorbs the wavelengths emitted by the sources 2, the areas of the contact surface 8 surrounding the detectors 3 provide an efficient optical shielding against ambient light (c.f. FIG. 2). Visible is also a multitude of optical barriers 4, which are formed by the main body 5 as opaque ridges 10 protruding from the contact surface 8 by a height of t3 (c.f. FIG. 5), which is in the order of 500 µm. The optical functionality of the optical barriers 4 is best understood with reference to FIGS. 25 and 26:

As FIG. 25 shows, the wavelength emitted by a light source 2 of the oximeter 1 may diffuse along several paths 27 through the tissue 24. However, as illustrated by the dotted arrows, part of the emitted light may propagate by multiple reflections in a layer 25 (not to scale in FIG. 25), which is always present during a measurement between the contact surface 8 and the skin 23, finally reaching the detector 3. This effect, which may be referred to as light piping, results in faulty measurements. By arranging multiple optical barriers 4 in or on the contact surface 8, propagation of the emitted wavelength in the layer 25 and up to the detector 3 can be suppressed.

FIG. 25 also illustrates, that at least two optical barriers 4 are necessary to efficiently suppress light piping for the case when the emitted light circumvents a first optical barrier 4 by traveling partly through tissue 24, as illustrated by the diffusion path 27a: even if this light re-enters the layer 25 after the first optical barrier 4, e.g. at the point of re-entrance 26 in FIG. 25, it will be stopped by the second optical barrier 4. Hence, only the diffusion path 27b will contribute to the measurement result. As a consequence, by applying multiple optical barriers 4, the oximeter 1 will become more sensitive to deeper layers of the tissue 24.

As an alternative or an addition to using a multitude of optical barriers 4, the angles at which light is emitted by the light source 2 and hence also at which this light is incident on the skin 23 may be limited by employing slit apertures 13 (or cylindrical lenses—not shown in FIG. 25). As can be understood from the illustration of FIG. 25, using such means, the initial reflections at the boundaries of the layer 25 may be suppressed by limiting the emission angles of the light source 2 to such angles at which no light propagation within the layer 25 is possible. Likewise, a slit aperture 13 may render the receptor 3 in FIG. 25 insensitive to light propagating with large reflections angles (i.e. large incidence angles on the surface 23) inside the layer 25. Thus the influence of light piping may be suppressed alternatively or additionally by limiting the angular range of emitted or received light rays, respectively.

FIG. 10 illustrates a cross-section of the oximeter 1 of FIG. 2 at the position C-C, which is also indicated in FIG. 11. As can be seen in FIG. 10, the slit aperture 13 is located inside the oximeter 1. The slit aperture 13 is separated from the transparent window 6, through which the four LEDs 2 emit light, by a transparent foil. Also visible in FIG. 10 is that the slit aperture 13 is smaller in size than the aperture defined by the window 6 below the aperture. This is particularly true for the dimension of the slit aperture 13 in the longitudinal direction x, as illustrated in FIG. 11.

As a result, the light pattern produced by the four LEDs on the skin 23 will a slim line oriented in the y-direction, i.e. the emission angles are mainly limited in the longitudinal direction 18, which is crucial for suppressing light propagation in the layer 25 between the oximeter 1 and the skin 23. As illustrated in FIG. 11, the slit apertures 13 are thus oriented transversal to the longitudinal axis 18 and also to all line-of-sights 15 used.

Figure 26:
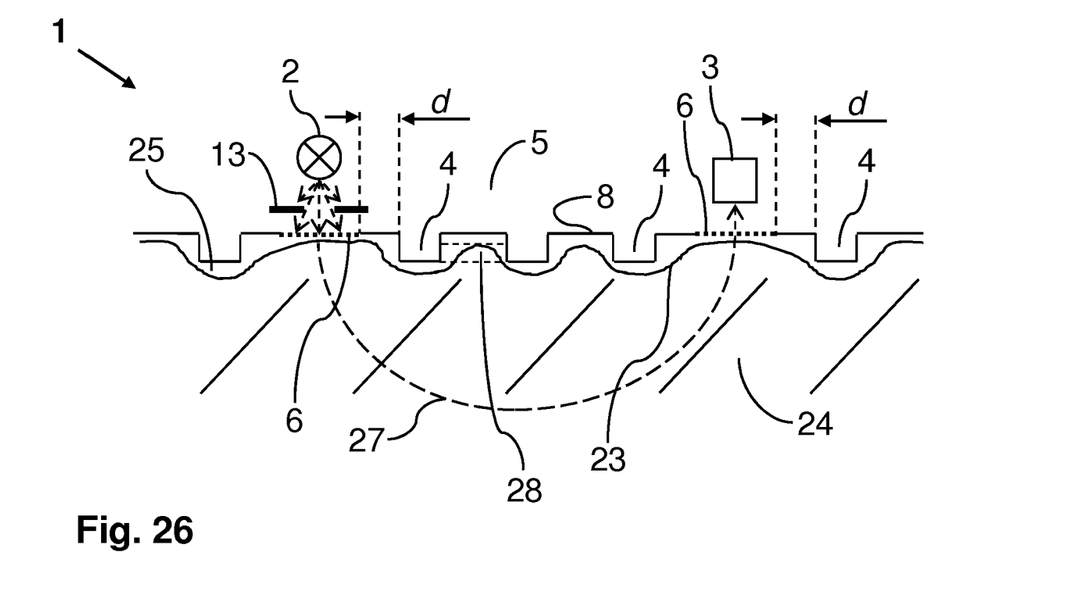
FIG. 26 illustrates the penetration of tissue into gaps between neighboring optical barriers such that a corrugated layer is formed between the surface of the medium and the contact surface of the apparatus.

A more realistic sketch of the measurement situation is given in FIG. 26: as illustrated, the skin 23 may actually follow the corrugation resulting from the optical barriers 4 in the contact surface 8. In fact, the skin 23 may actually penetrate in the space between the optical barriers 4, as indicated by the reference numeral 28 and the dashed horizontal lines in FIG. 26. As a result, although the layer 25 may still be present, it will no longer be flat but corrugated. In particular when keeping a gap d between a window 6 and neighboring optical barrier 4, as illustrated in FIG. 26, the skin can come into close vicinity to the window 6, such that a large portion of the emitted light enters the tissue 24, while the remaining part propagating in the unavoidable layer 25 can be effectively stopped by said neighboring optical barrier 4.

The outer shape of the contact surface 8 as well as the placement of the sources 3 and detectors 2 is symmetric with respect to both the longitudinal axis x as well as the transversal axis y, as is visible in both FIGS. 2 and 11. This also implies that the two detectors 3 are symmetrically arranged with respect to the light sources 2.

As the layout of the oximeter 1 in FIG. 11 shows in more detail, the oximeter 1 comprises two detectors 3 arranged on a longitudinal axis x and a total of 16 light sources 2. As light sources 2, LEDs with emission wavelength of 690, 760, 805, and 830 nm are employed. The oximeter 1 can thus measure with more than two different emission wavelengths along multiple source-detector-separations 22. As already explained, this redundancy allows application of a self-calibrating algorithm that cancels out variations in optical coupling or in characteristics of the sources and the detectors. The individual sources 2 are arranged in four columns of four LEDs each, while each column is oriented perpendicular to the longitudinal axis x. Between each source 2 and a detector 3, at least one optical barrier 4 is placed. For example, in FIG. 11, between the outermost right source 2 and the outermost left detector 3, a total of five optical barriers 4 are arranged.

For practical applications, the number of optical barriers 4 may be even higher, as illustrated in FIG. 2: in this embodiment, any line-of-sight 15 between a light source 2 and a detector 3 of the oximeter 1 which is used during a measurement is interrupted at least twice by two separate optical barriers 4. In fact, there exist sub-measurements that may be performed with the oximeter 1, in which all line-of-sights employed are interrupted at least four times by the multitude of optical barriers 4.

The lateral extensions 21 of the optical barriers 4 in the y-direction in the layout of FIG. 11 (and that of FIG. 2) are larger than the maximum distance 20 by which the light sources 2 of the oximeter 1 are separated in the y-direction. This ensures that all line-of-sights 15 can be efficiently blocked by the optical barriers 4.

Not visible in FIG. 2 are the slit apertures 13, because they are hidden behind the windows 6 and transparent ridges 9. As illustrated in FIGS. 1, 3-8, and 10, the transparent ridges 9 run across the windows 6, through which the measurement wavelength is emitted or received by the oximeter 1. From these figures, it may be further noted that the width of the transparent ridges 9 and neighboring opaque ridges 10 are equal; in fact, for the oximeter illustrated in FIG. 2, the cross-sections of the transparent and opaque ridges 9, 10 are identical to each other.

The oximeter shown in FIG. 2 also features gaps 16 between the single ridges. These gaps run transverse to a main direction of propagation of photons, which corresponds to the x-axis in FIG. 2. Preferably, these gaps 26 should run continuously and uninterruptedly over the full width of the contact surface 8, as illustrated in FIG. 2. These features enable the contact surface 8 to be used as a comb structure to comb the hair on the skin, with the transparent and opaque ridges 9, 10 acting as the teeth of the comb. Using this technique, hairs may be oriented along the gaps 16, such that light piping through the hairs is no longer in the direction of a source 3.

To reduce the overall stiffness of the main body 5 and hence allow easy bending, in particular around the y-axis, the cross-section of the oximeter 1 is reduced in the z-direction repeatedly along the x-axis from thickness t1 to thickness t2, as indicated by the numerals 11 in FIG. 5 (which is, however, not true to scale). Preferably, these thinnings 11 are formed end-to-end, i.e. they run along the complete width of the oximeter 1 in the y-direction.

Visible in FIG. 5 is also that the main body 5 of the oximeter is thinned towards its edges/its outline. This feature further improves the applicability and, as a result, the optical shielding against ambient light. As a result, the overall cross-section of the oximeter 1 shown in FIG. 5 resembles that of a chocolate bar. To achieve a substantial effect, the difference in thickness between t1 and t2 may be several millimeters. In other words, the corrugation on the upper side of the oximeter serves only mechanical purposes and is much larger than the corrugation on the contact surface 8, resulting from the optical barriers 4.

To prevent electromagnetic interference (EMI) from affecting the sensitive electronics of the oximeter, electromagnetic shieldings 12 are employed as shown in FIG. 5. Therefore both the sources 2 as well as the detectors 3 may be individually shielded against EMI.

Figure 12:
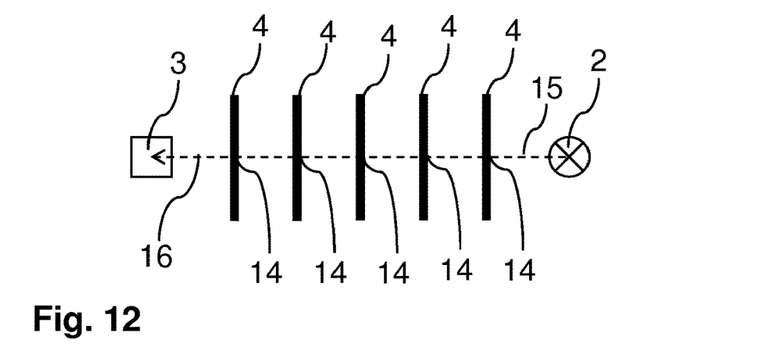
FIG. 12 illustrates a preferred arrangement of optical barriers according to the invention.
Figure 13:
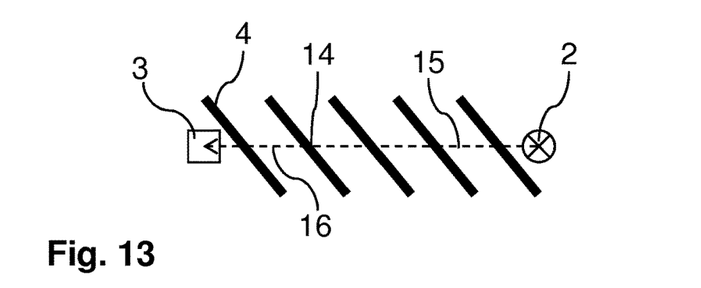
FIG. 13 illustrates another possible arrangement of optical barriers according to the invention.

Ideally, the optical barriers 4 should be arranged perpendicular to a line-of-sight 15 between a source 2 and a detector 3, as illustrated in FIG. 12. However, a non-perpendicular arrangement as shown in FIG. 13 is also possible and can lead to similarly high suppression of light piping. Nevertheless, at a point of intersection 14 between an optical barrier 4 and a line-of-sight 15, the angle of intersection between the optical barrier 4 and the line-of-sight 15 should be at least 45°, as illustrated by the examples of FIGS. 13 and 14.

Figure 14:
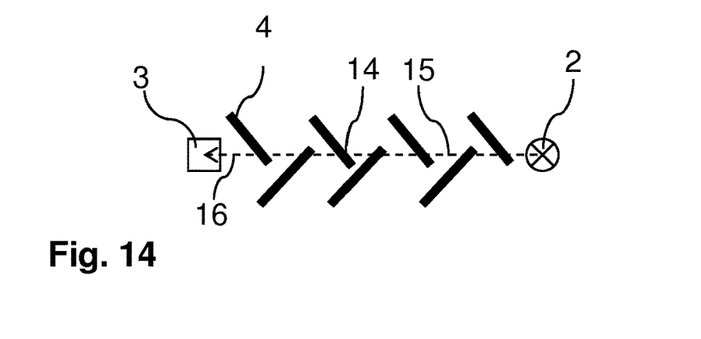
FIG. 14 illustrates yet another possible arrangement of optical barriers according to the invention.
Figure 15:
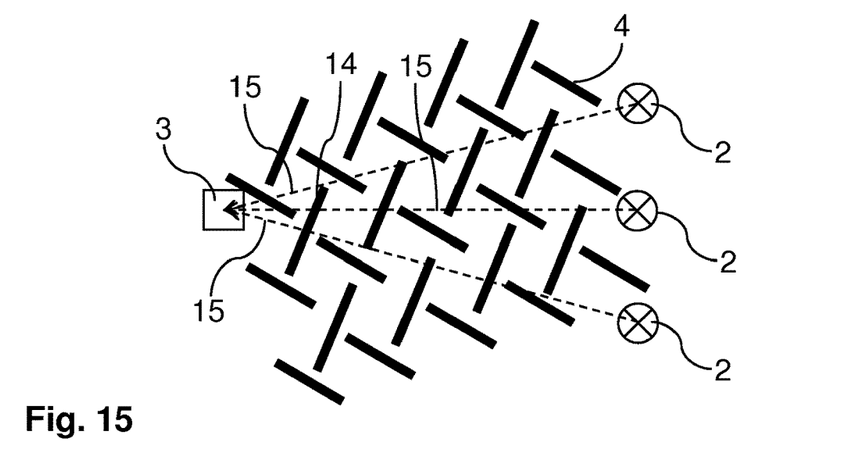
FIG. 15 illustrates yet another arrangement of optical barriers according to the invention.
Figure 16:
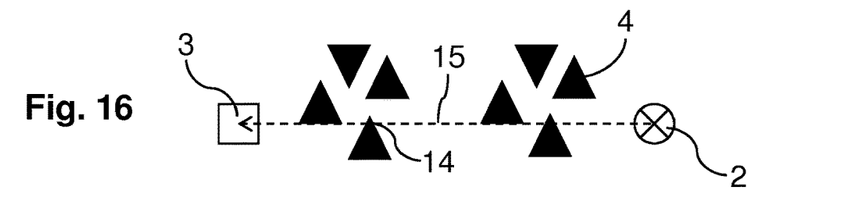
FIG. 16 illustrates a possible formation of optical barriers according to the invention.
Figure 17:
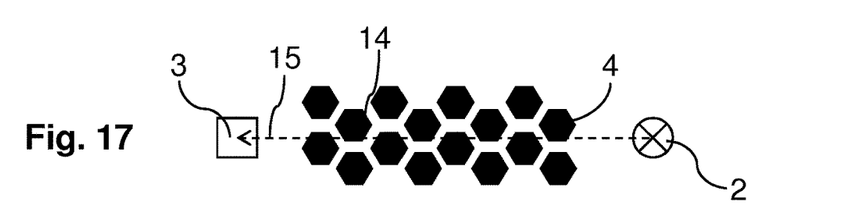
FIG. 17 illustrates another formation of optical barriers according to the invention.

The optical barriers may also be arranged in varying orientations as shown exemplarily in FIG. 14. Following this concept of using a multitude of optical barriers 4, manifold patterns may be conceived which all fulfill the technical function of interrupting the direct line-of-sight between a source and a detector at least once, preferably twice. Examples of possible patterns using optical barriers 4 of various shapes (triangular in FIG. 16, hexagonal in FIG. 17, circular in FIG. 18) to be formed in the contact surface 8 of the oximeter 1 are depicted in FIGS. 15 to 19. Different shapes may also be mixed, as illustrated in FIG. 19. Common to all of the patterns in FIG. 12-19 is that elevated areas (the dark structures denoted as optical barriers 4) are formed on the contact surface 8. Hence, when the oximeter 1 is placed on the skin 23 of a patient, the elevated structures will come in touch with the skin 23 and act as optical barriers 4, blocking the direct line-of-sights 15 parallel to the skin 23.

Figure 18:
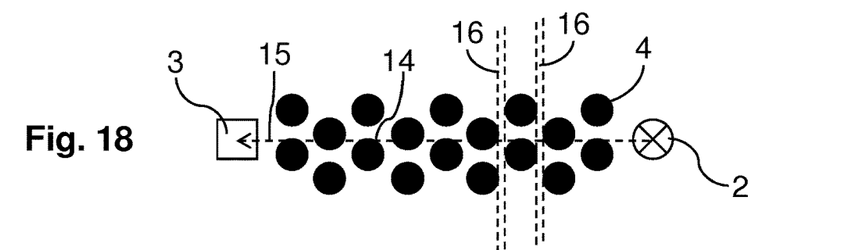
FIG. 18 illustrates yet another formation of optical barriers according to the invention.
Figure 19:
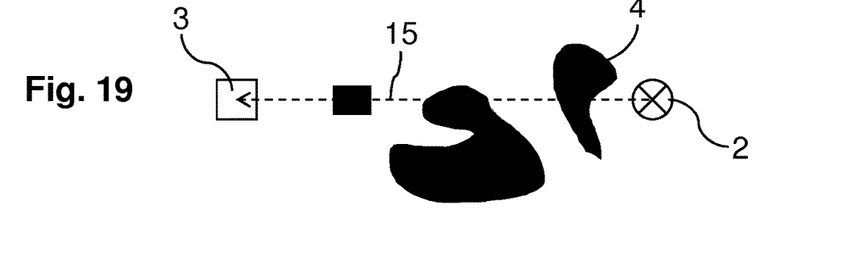
FIG. 19 illustrates the use of optical barriers of different shapes according to the invention.

As shown in FIG. 18, the comb effect described previously may be usable even if the optical barriers 4 are formed as (small-area) plateaus with intermediate gaps 16 and not as linear ridges 9, 10, as illustrated in FIG. 2.

The height difference between the top of the optical barriers 4 and the lower level of the gaps 16, which is donated as t3 in FIG. 5, may be in the range 100 . . . 1000 μm, depending on the width of the single optical barriers 4 in the x-y-plane.

Figure 20:
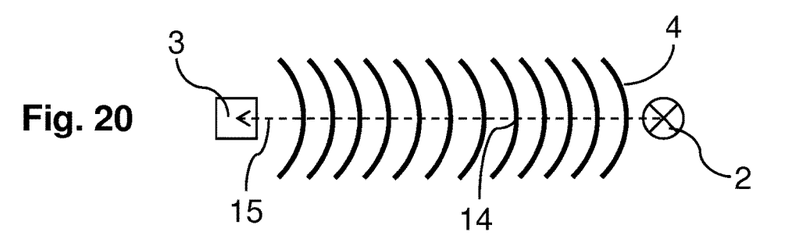
FIG. 20 illustrates a possible placement of optical barriers of circular shape according to the invention.
Figure 21:
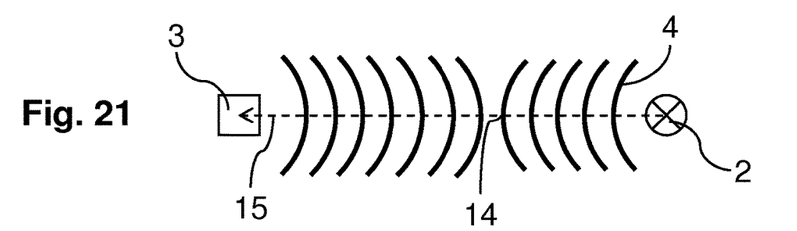
FIG. 21 illustrates another possible placement of optical barriers of circular shape according to the invention.

Yet another type of optical barriers 4 is shown in FIGS. 20 to 24: FIG. 20 depicts that optical barriers 4 may be arranged as circular walls with a constant radius of curvature, centered in the direction of the detector 3, and preferably placed at equal distances from each other. As illustrated in FIG. 21, it is also possible to center part of the optical barriers 4 towards a detector 3 and another part of the optical barriers 4 towards a source 2.

Figure 22:
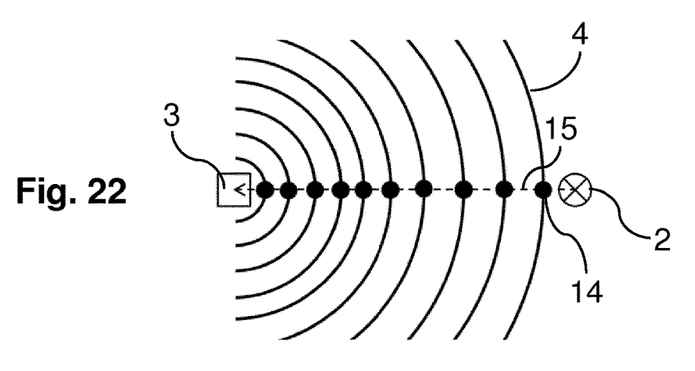
FIG. 22 illustrates yet another possible placement of optical barriers shaped as arcs according to the invention.
Figure 23:
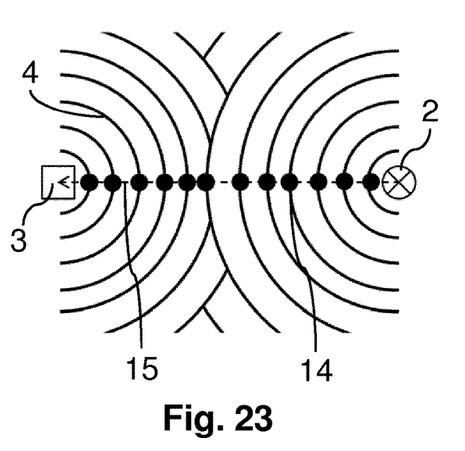
FIG. 23 illustrates the combination of two circular patterns of optical barriers according to the invention.
Figure 24:
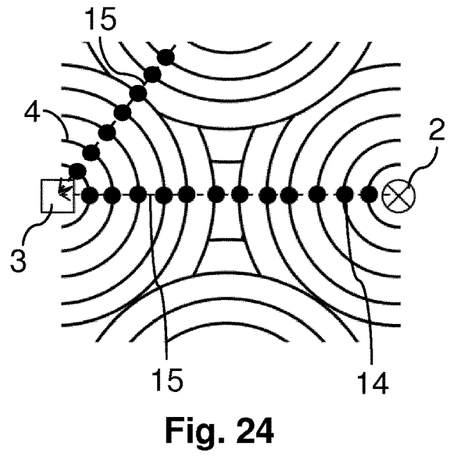
FIG. 24 illustrates the combination of multiple circular patterns of optical barriers, for the case where multiple sources are present, according to the invention.

Another possible arrangement is to center neighboring optical barriers 4 on a same center, namely for example on a detector 3, as shown in FIG. 22 and FIG. 23, or on an source 2, as shown in FIG. 23. When multiple detectors 3 or sources 2 are present, this concept can lead to patterns as the one shown in FIG. 24.

One advantage of using circular optical barriers 4 is that, at point of intersections 14 (indicated by black dots in FIG. 22-24) between an optical barrier 4 and a corresponding line-of-sight 15, the optical barriers can always be oriented at an intersecting angle of 90°, which is considered optimal for efficient suppression of light piping.

Another characteristic of the patterns shown in FIGS. 20 to 24 is that no matter from which direction light is propagating away from a source 2 or towards a detector 3, there are always several, for example at least 3, neighboring optical barriers 4 positioned at equal distances, which impede light propagation in the layer 25.

FIGS. 27 to 30 illustrate alternative embodiments for arranging a slit aperture 13 inside the main body 5 of apparatus 1 (c.f. FIG. 1). Shown in each of the FIGS. 27 to 30 is a section of the printed circuit board (PCB) 7 of FIG. 1, bearing a light source 2 and peripheral electronic components 29. To improve the electronic performance of the apparatus 1, an electromagnetic shielding 12 covers the light source 2 as well as the electronic components 29 in direct vicinity of the light source 2.

Figure 27:
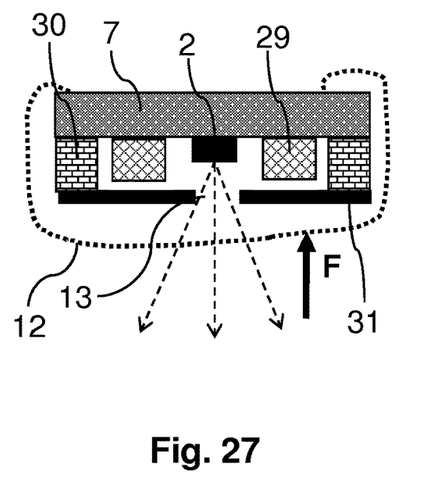
FIG. 27 illustrates an arrangement of a slit aperture on a printed circuit board, inside the apparatus.

In FIG. 27, the em-shielding 12 consists of a mesh formed from copper wires. The mesh, illustrated by the dotted line, produces a Faraday shield and offers repeated perforations through which the light emitted by the light source 2 can pass with only minor attenuation. The em-shielding 12 is electrically connected to a ground potential provided on the PCB 7. Excellent signal quality is particularly achievable, if a similar em-shielding 12 as the one shown in FIG. 27 covers a detector 3 of the apparatus 1 (c.f. FIG. 1).

To avoid an electrical short-circuit between the em-shielding 12 and the light source 2 or the electronic components 29 when a force F is acting on the em-shielding 12 during a measurement, the em-shielding 12 in FIG. 27 is insulated from the light source 2 by a frame 30 bearing an opaque sheet 31. Both the frame 30 and the sheet 31 are made from an insulating material. Alternatively, the sheet 31 may be made from a conducting material, but in this case, care must be taken to maintain an air gap between the sheet 31 and the components 29 at all time.

A slit has been laser-cut into the sheet 31 to form an optical slit aperture 13. As is visible from the cross-sectional view of FIG. 27, the slit aperture 13 is positioned within the em-shielding 12. This approach ensures an improved electronic performance, a stable aperture position during the measurement (since the slit aperture's 13 shape or position is unaffected when pressure is applied to the contact surface 8 of the apparatus 1 (c.f. FIG. 1)) and a compact height of the apparatus 1 in the z-direction.

Figure 28:
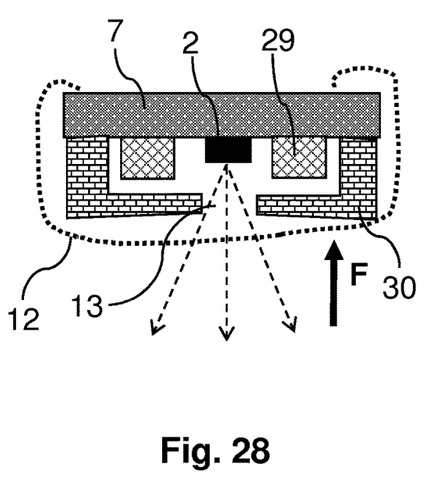
FIG. 28 illustrates an alternative internal slit aperture arrangement.

In the example of FIG. 28, the combination of sheet 31 and frame 30 has been replaced by a frame 30 of more complex geometry, which forms the slit aperture 13. The frame 30 is made of an insulator material thus insulating the em-shielding 12 in the form of a mesh from the components 29 and the light source 2.

Figure 30:
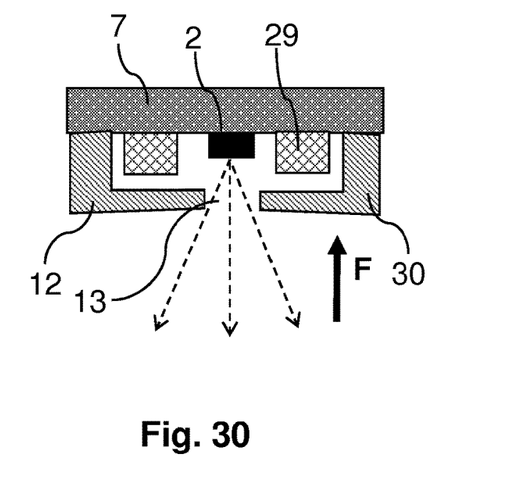
FIG. 30 illustrates a simplified slit aperture arrangement.

If such a frame 30 is made of high rigidity, for example by milling it out of a piece of bulk material, an arrangement as the one shown in FIG. 30, can be achieved. In this particular embodiment, the frame 30 forms the slit aperture 13 as in the previous example of FIG. 28. But in addition, the frame 30 now also forms the em-shiedling 12. For this purpose, the frame 30 may be made from a conducting material, e.g. in the form of a metal structure, or alternatively, it may be made from an insulating material but featuring a conductive coating. In the latter case, the em-shielding 12 is provided by the conductive coating. In this case, it is preferably, if the coating is provided only on the outer surfaces of the frame 30, since the frame itself may then insulate the conductive coating and thus the em-shielding 12 from the light source 2 or detector 3, respectively. Although no mesh is necessary in the embodiment of FIG. 30, the slit aperture 13 is still formed inside the em-shielding 12, provided by the frame 30.

Figure 29:
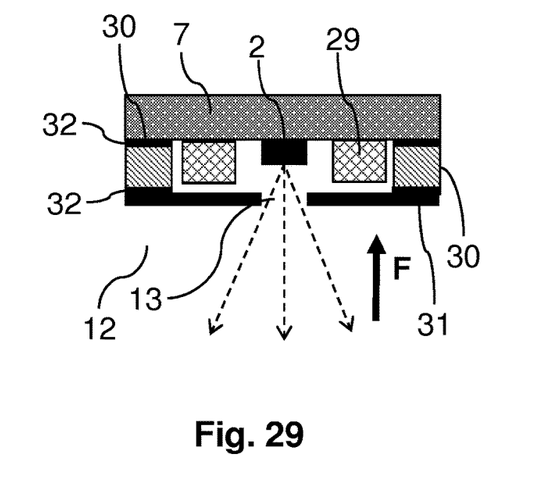
FIG. 29 illustrates yet another possible arrangement of on an internal slit aperture, and finally

Finally, FIG. 29 shows yet another possible way of arranging a slit aperture 13 inside the apparatus 1, according to the invention. In this embodiment, the frame 30 as well as the sheet 31 are made from a conductive material and electrically connected to each other and the PCB 7 by conductive joints 32, e.g. a solder line or conductive glue, respectively. By this approach, the sheet 31 may form the slit aperture 13, as shown in FIG. 29, and the sheet 31 together with the frame 30 may form the em-shieldling 12. Thus, no additional mesh is required, as was the case in FIGS. 27 and 28. In a design such as the one shown in FIG. 29, care should be taken, that the sheet 31 is rigid enough such that the air gap between the sheet 31 and the components 29 that is visible in FIG. 29 is maintained when a typical force F is applied onto the sheet 31 during a measurement.

In conclusion, a spectrophotometric apparatus 1 is proposed for determining optical parameters in a scattering medium 4 based on the measurement of attenuation of light propagating through said medium 4 by diffusion. To eliminate the detrimental effect of light being guided in an intermediate optical layer 25 between a surface 23 of the medium 4 and a contact surface 8 of the apparatus 1, either a multitude of optical barriers 4 may be formed in the contact surface 8 or the angular range over which light is emitted or received by the apparatus 1 may be limited by appropriate means 13. With both of these alternative approaches, light propagation in the intermediate layer 25 can be suppressed, leading to increased measurement accuracy. The invention is particularly beneficial for building an oximeter 1 with improved precision. Further aspects of the invention concern features for improving the applicability of the apparatus 1 on curved surfaces 23 such as the strongly curved skulls of neonates.

LIST OF REFERENCE NUMERALS 1 apparatus (e.g. an oximeter)
2 light source
3 detector
4 optical barrier
5 main body (opaque)
6 window
7 printed circuit board
8 contact surface
9 transparent ridge
10 opaque ridge
11 thinning
12 electromagnetic shielding
13 slit aperture
14 point of intersection
15 line-of-sight
16 gap
17 indentation
18 longitudinal axis
19 transversal axis 20 lateral length
21 transverse separation (of light sources)
22 source-detector-separation
23 surface of the medium (e.g. skin)
24 scattering medium (e.g. tissue)
25 layer
26 point of re-entrance (into 25)
27 diffusion path
28 penetration (of skin in between 4)
29 electronic component
30 frame
31 sheet (opaque)
32 conductive joints

The invention claimed is:

1. An apparatus (1) for measuring optical parameters in a scattering medium (24), the apparatus comprising:
at least one light source (2) emitting at least one wavelength;
at least one detector (3) for detecting said wavelength;
said at least one light source (2) and said at least one detector (3) emit and receive light, respectively, through a contact surface (8) being in contact with a surface (23) of the medium (24) during a measurement;
the contact surface (8) is formed by a main body (5) of a soft material, such that the contact surface is bendable;
the at least one light source (2) and the at least one detector (3) are configured to emit and receive photons, respectively, through windows (6) embedded in the contact surface (8);
a slit aperture (13) for limiting angles at which light rays which are emitted by said at least one light source (2) exit said contact surface (8) or at which light rays received by said at least one detector (3) re-enter said contact surface (8), such that propagation of said wavelength through the layer (25) between the contact surface (8) and the surface (23) of the medium (24) is suppressed, and
said slit aperture (13) is located inside the apparatus and is smaller than an aperture defined by a corresponding one of the windows (6).

2. The apparatus (1) according to claim 1, wherein on or in said contact surface (8), at least two optical barriers (4) are arranged such that propagation of said wavelength through a layer (25) between the contact surface (8) and the surface (23) of the medium (24) is suppressed.

3. The apparatus (1) according to claim 2, wherein said apparatus (1) comprises a multitude of slit apertures (13) for limiting said angles.

4. The apparatus (1) according to claim 3, wherein at least one of the at least one light source (2) or the at least one detector (3) are covered by an electromagnetic shielding (12), and said slit apertures are located within said electromagnetic shielding (12).

5. The apparatus (1) according to claim 2, wherein at least one of (a) the at least one light source comprises at least two light sources (2) or (b) the at least one detector comprises at least two detectors (3) such that the apparatus (1) features at least two different line-of-sights (15) which may be used during a measurement.

6. The apparatus (1) according to claim 5, wherein said optical barriers (4) interrupt each of the at least two line-of-sights (15) at least once.

7. The apparatus (1) according to claim 2, wherein said optical barriers (4) are formed as walls or ridges (10) protruding from said contact surface (4), a height of said optical barriers (5) above said contact surface (4) is less than 5000 µm, said optical barriers (4) are shaped exclusively with angles of more than 90°.

8. The apparatus (1) according to claim 2, wherein at least one of: (a) said optical barriers (4) have a width in a direction of a corresponding line-of-sight (15) of more than 100 µm, (b) said optical barriers (4) are formed as corrugations, (c) a minimum distance between neighboring optical barriers (4) is larger than a height of said neighboring optical barriers (4), or (d) said optical barriers (4) are at least one of made from a material which at least one of absorbs said wavelength, is porous, has a surface that is rough or optically matt or said contact surface (8) is at least one of porous, optically matt, or absorbs said wavelength.

9. The apparatus (1) according to claim 2, wherein at least 10% of the line-of-sight (15) along the contact surface (8) is occupied by said optical barriers (4).

10. The apparatus (1) according to claim 2, wherein said slit aperture is oriented such that said angles are limited in a direction of a corresponding line-of-sight (15).

11. The apparatus (1) according to claim 2, wherein said slit aperture (13) is located at a distance from said windows (6).

12. The apparatus (1) according to claim 11, wherein said optical barriers (4) are spaced apart from said windows (6) in a direction of the corresponding line-of-sight (15).

13. The apparatus (1) according to claim 2, wherein at least a subset of the light sources (2) and the detectors (3) are linearly arranged along a longitudinal axis (18), such that for photons emitted by any of said linearly arranged light sources (2) and reaching one of said detectors (3), a main direction of propagation coincides with said longitudinal axis (18), and all of said optical barriers (4) are oriented at an angle of more than 45° to said longitudinal axis (18).

14. The apparatus (1) according to claim 2, wherein said apparatus (1) is an oximeter for measuring tissue oxygenation, and said surface (23) of the medium (24) is a tissue surface (23).

15. The apparatus (1) according to claim 14, wherein said at least one light source (2) emits at least two different wavelengths, and said optical barriers (4) or said slit aperture (13) is arranged such that propagation of said at least two different wavelengths through the layer (25) is suppressed.

16. The apparatus (1) according to claim 2, wherein the optical barriers are shaped with rounded edges, and at points of intersections (14) between said optical barriers (4) and the line-of-sight (15), said optical barriers (4) are oriented at an angle of intersection of more than 45° to the line-of-sight (15) being intersected.

17. The apparatus (1) according to claim 2, wherein said optical barriers (4) are arranged between said at least one light source (2) and said at least one detector (3), such that said optical barriers (4) interrupt a line-of-sight (15) along the contact surface (8) between said at least one light source (2) and said at least one detector (3) at least twice.

18. The apparatus (1) according to claim 1, wherein at least one of said windows (6) includes a transparent ridge (9) facing the surface (23), said transparent ridge (9) running in a direction transverse to a main direction of propagation of said photons emitted by said at least one light source (2) and reaching said at least one detector (3).

19. The apparatus (1) according to claim 1, wherein said main body (5) is formed of a material that is opaque to said wavelength, said main body (5) at least one of carrying or encapsulating said at least one light source (2) and said at least one detector (3), and said main body (5) forms at least one of said optical barriers (4) or said slit apertures, or said main body (5) includes thinnings (11), and said thinnings (11) run across a full width of the apparatus (1) in a transversal direction (19).

20. The apparatus (1) according to claim 1, wherein the contact surface (8), in a relaxed equilibrium state thereof, has a first curvature along a first axis (19) of the apparatus (1), and the contact surface (8) has a second curvature along a second axis.

\* \* \* \* \*